United States Patent [19]

DeLuca et al.

[11] 4,358,406

[45] Nov. 9, 1982

[54] 26,26,26,27,27,27-HEXAFLUORO-1α,25-DIHYDROXYCHOLECALCIFEROL AND PROCESS FOR PREPARING SAME

[75] Inventors: Hector F. DeLuca; Yoko Tanaka, both of Madison, Wis.; Nobuo Ikekawa, Musashinoshi; Yoshiro Kobayashi, Tokyo, both of Japan

[73] Assignee: Wisconsin Alumni Research Foundation, Madison, Wis.

[21] Appl. No.: 286,790

[22] Filed: Jul. 27, 1981

[51] Int. Cl.$^3$ .................... C07J 17/00; C07C 35/21; C07C 69/013
[52] U.S. Cl. .................. 260/239.55 R; 260/397.2; 560/256; 568/819
[58] Field of Search ................ 260/397.2, 239.55 R

[56] References Cited

U.S. PATENT DOCUMENTS 4,226,788  10/1980  DeLuca et al. ............... 260/397.2
4,248,791   2/1981  DeLuca et al. ............... 260/397.2

*Primary Examiner*—Elbert L. Roberts
*Attorney, Agent, or Firm*—Howard W. Bremer

[57] ABSTRACT

This invention provides a new derivative of vitamin D, 26,26,26,27,27,27-hexafluoro-1α,25-dihydroxycholecalciferol, a process for preparing the same, and novel intermediate compounds.

The compound is characterized by vitamin D-like activity substantially greater than that exhibited by 1α,25-dihydroxycholecalciferol which is considered to be the active hormonal form of vitamin D. The compound would find ready application as a substitute for vitamin D and in the treatment of or prophylaxis for disease states evincing metabolic calcium and phosphorous deficiencies or imbalances.

9 Claims, No Drawings

26,26,26,27,27,27-HEXAFLUORO-1α,25-DIHYDROXYCHOLECALCIFEROL AND PROCESS FOR PREPARING SAME

The invention described herein was made in the course of work under a grant or award from the Department of Health and Human Services, and U.S. Japan Cooperative Grant INT-76-05793 and IPA No. 0001 awarded by the National Science Foundation.

DESCRIPTION

1. Technical Field

This invention relates to a compound which is characterized by vitamin D-like activity.

More specifically this invention relates to a derivative of vitamin $D_3$, to a method for preparing such compounds and to novel intermediates generated during such process.

Vitamin $D_3$ is a well-known agent for the control of calcium and phosphorous homeostasis. In the normal animal or human this compound is known to stimulate intestinal calcium transport and bone-calcium mobilization and is effective in preventing rickets.

It is also now well known that to be effective, vitamin $D_3$ must be converted in vivo to its hydroxylated forms. For example, the vitamin is first hydroxylated in the liver to form 25-hydroxy-vitamin $D_3$ and is further hydroxylated in the kidney to produce 1α,25-dihydroxy vitamin $D_3$ or 24,25-dihydroxy vitamin $D_3$. The 1α-hydroxylated form of the vitamin is generally considered to be the physiologically active or hormonal form of the vitamin and to be responsible for what are termed the vitamin D-like activities, such as increasing intestinal absorption of calcium and phosphate, mobilizing bone mineral, and retaining calcium in the kidneys.

2. Background Art

Since the discovery of biologically active metabolites of vitamin D there has been much interest in the preparation of structural analogs of these metabolites, because such compounds may represent useful therapeutic agents for the the treatment of diseases resulting from calcium metabolism disorders. A variety of vitamin D-like compounds have been synthesized. See, for example, U.S. Pat. Nos. 3,741,996 directed to 1α-hydroxychloecalciferol; 3,907,843 directed to 1α-hydroxyergocalciferol; 3,786,062 directed to 22-dehydro-25-hydroxycholecalciferol; 3,906,014 directed to 3-deoxy-1α-hydroxycholecalciferol; and 4,069,321 directed to the preparation of various side chain-fluorinated vitamin $D_3$ derivatives and side chain-fluorinated vitamin $D_3$ derivatives and side chain-fluorinated dihydrotachysterol analogs.

A fluoro derivative of the accepted hormonal form of the vitamin, 1,25-dihydroxycholecalciferol (1,25-$(OH)_2D_3$) of particular interest is 24,24-difluoro-1,25-$(OH)_2D_3$ because it is characterized by at least as great if not greater activity than 1,25-$(OH)_2D_3$. (See U.S. Pat. No. 4,201,881.)

Also of interest is the 26,26,26,27,27,27-hexafluoro derivative of 25-hydroxycholecalciferol (see U.S. Pat. No. 4,248,791) which exhibits greater vitamin D-like activity than 25-hydroxycholecalciferol.

DISCLOSURE OF INVENTION

A new derivative of vitamin D has now been prepared which is characterized by substantially greater vitamin D-like activity than the hormonal form of the vitamin, 1,25-$(OH)_2D_3$ as measured by its ability to stimulate calcium transport in the intestine, to mobilize calcium from bone (serum calcium level increase) and in its antirachitic activity as measured by the rat line test.

This derivative has been identified as 26,26,26,27,27,27-hexafluoro-1,25-dihydroxycholecalciferol (26,26,26,27,27,27-$F_6$-1α,25-$(OH_2)D_3$).

The exceptionally high vitamin D-like activity of the compound indicates its ready application as a substitute for vitamin D in its various known applications and as a therapeutic agent in the treatment of such diseases as hypoparathyroidism, pseudohypoparathyroidism, renal osteodystrophy, osteoporosis and other types of bone disorders symptomatic of calcium and phosphorous imbalance. Other potential applications would be in the treatment of milk fever disease in cattle, leg weakness in turkeys, chickens and other poults, and as a prophylactic agent against leg weakness condition in other domestic animals.

BEST MODE FOR CARRYING OUT THE INVENTION

The compounds of this invention can be readily synthesized in accordance with the following schematic and description utilizing as the starting material 26,26,26,27,27,27-hexafluoro-25-hydroxycholesterol-3-THP ether (U.S. Pat. No. 4,248,791). In the schematic and the following description like compounds are identified by like numbers.

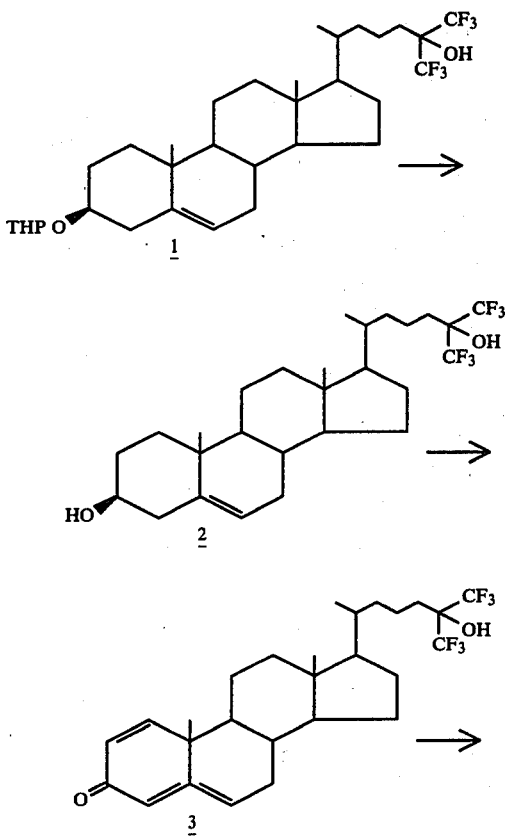

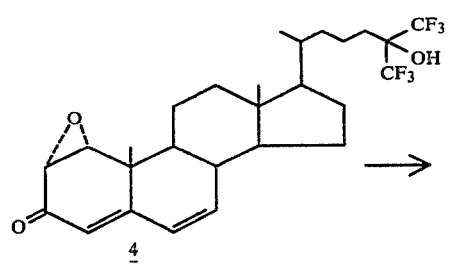

4

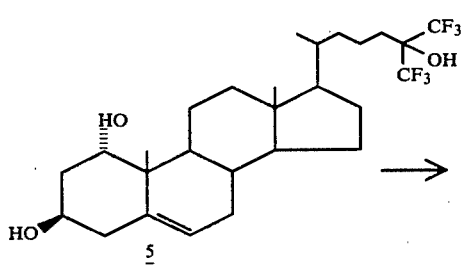

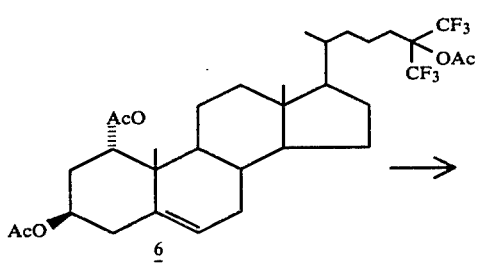

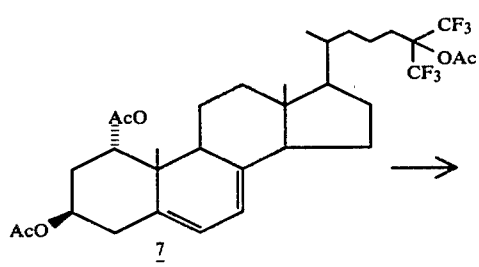

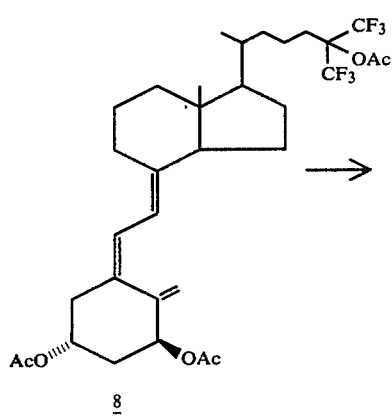

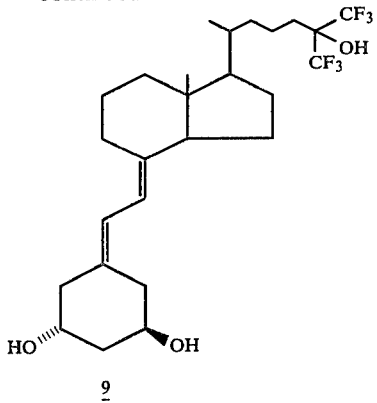

(1) was hydrolyzed by p-toluenesulfonic acid to give 3-ol (2), which was oxidized with dichlorodicyanobenzoquinone (DDQ). The 1,4,6-trien-3-one (3) was obtained in 55% yield. Treatment of the trienone 3 with alkaline hydrogen peroxide gave the 1,2-epoxide (4) (97% yield), which was reduced with lithium metal and ammonium chloride in liquid ammonia-tetrahydrofuran yielding 1-hydroxy compound (5) (65%). After acetylation, the triacetate (6) was treated with N-bromosuccinimide and then with collidine to afford the 5,7-diene (7). The 5,7-diene was irradiated with a medium pressure mercury lamp in benzene-EtOH followed by themal isomerization in refluxing benzene-EtOH to give the hexafluoro-1,25-diacetoxyvitamin $D_3$ (8), which was then hydrolyzed to the corresponding hexafluoro-1,25,dihydroxy vitamin $D_3$ (9).

Synthesis of
26,26,26,27,27,27-hexafluoro-1α,25-dihydroxycholecalciferol 26,26,26,27,27,27-Hexafluoro-25-hydroxycholesterol (2)

The THP ether (1) was synthesized according to the procedure of Y. Kobayashi, T. Taguchi, N. Kanuma, N. Ikekawa and J. Oshida, J. C. S. Chem. Comm. 459 (1980). After treatment of (1) (345 mg) with p-toluenesulfonic acid (10 mg) in a mixture of $CH_2Cl_2$ (15 ml) and MeOH (8 ml) at room temperature for 2 hr, $NaHCO_3$ solution was added to the reaction mixture which was then extracted with $CH_2Cl_2$. The extract was recrystallized from benzene-cyclohexane to give 212 mg of (2), mp 180°–181° C., MS m/e 510(M+), 495, 492, 477, 255, 213; NMR (acetone-$D_6$-$D_2O$)δ0.71(s, 18-$H_3$), 0.95(d, J=6 Hz, 21-$H_3$), 1.02(s, 19-$H_3$), 3.40 (1H, m, 3-H), 5.32(1H, m, 6-H). Anal. Calcd. for $C_{27}H_{40}F_6O_2$: C, 63.51: H, 7.90;F, 22.33. Found: C, 63.72; H, 7.84; F, 22.54.

26,26,26,27,27,27-Hexafluoro-25-hydroxycholest-1,4,6-trien-3-one (3)

A mixture of (2) (893 mg) and DDQ (2.2 g) in dioxane (50 ml) was stirred for 15 hr at 80°–90° C. and then refluxed for 4 hr. After cooling to room temperature the precipitate was filtered off and the filtrate was diluted with ether which was successively washed with 1 N-KOH and brine. The extract was purified by silica gel column (AcOEt-n-hexane, 1:20 to give 490 mg (55%) of the trienone (3); mp 166°–168° C. (from AcOEt-cyclohexane), MS m/e 504(M+), 489; IR(KBr), 3180, 1650, 1595 cm$^{-1}$; NMR(CDCl$_3$)δ0.72(s, 18-H$_3$), 0.95(d, J=6 Hz, 21-H$_3$), 1.18 (s, 19-H$_3$), 5.88–6.33(4H, m, 2-,4-,6- and 7-H), 7.04(1H, d, J=10 Hz, 1-H). Anal. Calcd., For C$_{27}$H$_{34}$F$_6$O$_2$; C, 64.27; H, 6.79; F, 22.59. Found, C, 64.17; H, 6.81; F, 22.34.

26,26,26,27,27,27-Hexafluoro-25-hydroxy-1α,2α-epoxy-cholest-4,6-dien-3-one (4)

To a solution of 27 ml of NaOH and 1 ml of 30% H$_2$O$_2$ in degassed MeOH (20 ml) was added a THF solution (10 ml) of 497 mg of the trienone (3) and then the reaction mixture was stirred for 20 hr at room temperature. The reaction mixture was diluted with brine and extracted with ether. The ethereal extract was submitted to silica gel column chromatography (AcOEt-n-hexane, 1:4) to give 499 mg (97%) of the epoxide (4): mp 181°–184° C. (from AcOEt-cyclohexane), MS m/e 520(M$^+$), 505, 503; NMR(CDCl$_3$)δ0.70(s, 18-H$_3$), 0.95(d, J=6 Hz, 21-H$_3$), 1.00(s, 19-H$_3$), 3.45 (1H, m, 2-H), 3.62(1H, d, J=6 Hz, 1-H), 4.10(1H, s, OH), 5.62(1H, bs, 4-H), 6.04(2H, s, 6- and 7-H).

26,26,26,27,27,27-Hexafluoro-1α,25-dihydroxycholesterol (5)

To a solution of 1.2 g of lithium in 80 ml of liquid ammonia (distilled over Na) was added 443 mg of the epoxide (4) in THF (70 ml) dropwise during 1 hr under dry ice-acetone bath cooling and then the reaction mixture was stirred for 1 hr at reflux. The reaction mixture was recooled by dry ice-acetone bath and to this was added solid NH$_4$Cl (12 g) in small portions during 1 hr, then refluxed for 3 hr. After bubbling argon gas to remove NH$_3$, water was added to the reaction mixture and this was extracted with AcOEt. The extract was submitted to silica gel column chromatography. The fraction eluted with n-hexane and AcOEt (1:2) afforded 274 mg (65%) of the triol (5), mp 201°–202° C. (from CHCl$_3$), MS Calcd. for C$_{27}$H$_{40}$F$_6$O$_3$: 526.2879. Found: 526.2878. NMR(CDCl$_3$) and acetone-D$_6$δ0.69(s, 18-H$_3$), 0.93(d, J=6 Hz, 21-H$_3$), 1.03(s, 19-H$_3$), 3.83(1H, m, 1-H), 4.00(1H, m, 3-H), 5.53(1H, m, 6-H).

26,26,26,27,27,27-Hexafluoro-1α,25-dihydroxycholesterol triacetate (6)

A solution of 216 mg of the triol (5) and catalytic amounts (ca 20 mg) of 4-dimethylaminopyridine in acetic anhydride (1.5 ml) and pyridine (3 ml) was stirred for 20 hr at room temperature. After the reaction mixture was concentrated in vacuo, the residue was chromatographed on silica gel (n-hexane-AcOEt, 10:1) to give 263 mg (98%) of the triacetate (6), which was dried at 70° C. (5 mm Hg) for 20 hr. 6: glass; MS m/e 592(M$^+$-AcOH), 532(M$^+$-2AcOH), 517, 413, 253; NMR(CDCl$_3$)δ0.66(s, 18-H$_3$, 0.94(d, J=6 Hz, 21-H), 1.10(s, 19-H$_3$)2.03, 2.06 and 2.16(9H, each s, acetyl), 4.98(1H, m, 3-H), 5.06(1H, m, 1-H), 5.53(1H, m, 6-H).

26,26,26,27,27,27-Hexafluoro-1α,3β,25-triacetoxycholest-5,7-diene (7)

N-bromosuccinimide (14 mg) was added to a refluxing solution of 35 mg of triacetate (6) in 2 ml of CCl$_4$ and the reaction mixture was refluxed further under argon atmosphere. After cooling in an ice-water bath, the resulting precipitate was filtered off. The filtrate was evaporated to dryness below 40° C. The residue is xylene (1 ml) was added dropwise to a refluxing solution of xylene (1.5 ml) and s-collidine (0.5 ml) and refluxing was continued under argon atmosphere for 20 min. The reaction mixture was extracted with AcOEt, washed with 2 N-HCl, sat. NaHCO$_3$, brine and the solution was dried over MgSO$_4$. After removal of the solvent, the residue was treated with a catalytic amount of pTsOH in acetone (10 ml) at room temperature for 16 hr under argon in the dark. The mixture was extracted with AcOEt and the extract was washed with sat. NaHCO$_3$ and brine, and then dried over MgSO$_4$. Removal of the solvent gave a crude 5,7-diene, which was purified by preparative TLC developed twice with a solvent of n-hexane-AcOEt (10:1). The band of Rf value 0.26 was scraped off and eluted with AcOEt. Removal of the solvent gave 8.8 mg (25%) of the product (7); UV-(EtOH)λ$_{max}$, 294, 282, 272 nm.

26,26,26,27,27,27-Hexafluoro-1α,25-dihydroxyvitamin D$_3$ triacetate (8)

A solution of the 5,7-diene (7) (8.8 mg) in benzene (90 ml) and EtOH (40 ml) was irradiated with a medium pressure mercury lamp through a Vycor filter for 2.5 min with ice-cooling under argon. Then, the mixture was refluxed for 1 hr under argon. Evaporation of the solvent gave a crude vitamin D derivative, which was submitted to preparative TLC (developed twice with hexane-AcOEt (10:1). The band of Rf value 0.36 was scraped off and eluted with AcOEt. Removal of the solvent gave a pure product (8) (1.6 mg) (25%), UV (EtOH)λ$_{max}$, 264.5,λ$_{min}$ 228 nm.

26,26,26,27,27,27-Hexafluoro-1,25-dihydroxyvitamin D$_3$ (9)

A solution of the triacetate (8) (1.6 mg) in 5% KOH-MeOH (2 ml) and THF (2 ml) was stirred at room temperature under argon in the dark for 14 hr. The reaction mixture was acidified with 2 N HCl and extracted twice with AcOEt. The extract was washed with sat. NaHCO$_3$ and brine, and dried over MgSO$_4$. Removal of the solvent gave the product (9) (1.13 mg, 90%) which was purified by HPLC. Compound (9), UV (EtOH)λ$_{max}$ 264.5 nm,λ$_{min}$ 228 nm; MS m/e 524(M$^+$), 506, 488, 473, 462, 383, 287, 269, 251, 152, 134.

The 26,26,26,27,27,27-F$_6$-1,25-(OH)$_2$D$_3$ product can, if desired be obtained in crystalline form by dissolution in a suitable solvent or solvent system, e.g. ether, ether-hexane, methanolether, ethylacetate-alkane, and then removing the solvent(s) by evaporation or other means as is well known.

Also, if desired, the 5,7-diene (7) can be hydrolyzed in accordance with the foregoing procedure or other mild basic hydrolysis procedures well known in the art prior to irradiation to convert the acetoxy substituents to hydroxyl.

Biological Activity

The biological potency of 26,26,26,27,27,27-F$_6$-1,25(OH)$_2$D$_3$ was established through appropriate in vivo assays in the rat in comparison with the biological activity of 1,25-(OH)$_2$D$_3$.

Male weanling rats purchased from Holtzman Co. (Madison, WI) were fed, ad libitum, water and either a low phosphorus, high calcium, vitamin D-deficient diet (rachitogenic diet) as described by Tanaka and DeLuca (Proc. Natl. Acad. Sci. USA (1974) 71, 1040) or low calcium, adequate phosphorus, vitamin D-deficient diet as described by Suda et al (J. Nutrition (1970) 100, 1049) for 3 weeks.

Rats that had been fed the rachitogenic diet for 3 weeks were divided into five groups of 5-6 rats each and were given either 3,25 pmol or 13 pmol of either 26,26,26,27,27,27-$F_6$-1,25-$(OH)_2D_3$ or 1,25-$(OH)_2D_3$ dissolved in 0.1 ml mixture of propylene glycol-ethanol (95:5), subcutaneously, daily for 7 days. Rats in the control group were given 0.1 ml of the propylene glycol-ethanol vehicle in the same manner. Twenty-four hours after the last dose, they were killed by decapitation, the blood was collected for measurement of concentration of serum inorganic phosphorus, their duodena were removed to measure the intestinal calcium transport activity and their radii and ulnae were removed for measurement of the antirachitic activity as described below.

Intestinal Calcium Transport

Intestinal calcium transport activity in response to either compound was measured by the method described by Martin and DeLuca (Am. J. Physiol. (1969) 216, 1351). Results are shown in Table 1, first column.

Measurement of Serum Inorganic Phosphorus

Blood was centrifuged immediately to yield serum. Ten percent trichloroacetic acid was added to the serum, and the supernatant recovered after centrifugation was analyzed by the method as described by P. S. Chen et al (Anal. Chem. (1956)28, 1756). Results are shown in Table 1, second column.

Antirachitic Activity

Radii and ulnae of rats were removed, split lengthwise, and stained in 1.5% silver nitrate solution. Evaluation of antirachitic activity was achieved in accordance with rat line test described in U.S. Pharmacopoeia (15th Edition, Mack Publishing Co., Easton, PA). Results are shown in Table 1, third column.

TABLE 1

| Compound | Amount (pmol/day) | Intestinal calcium transport (Ca serosal/Ca mucosal) | Serum inorganic phosphorus (mg/100 ml) | Antirachitic activity (units) |
|---|---|---|---|---|
| vehicle | | $3.5 \pm 0.3^{*a}$ | $1.7 \pm 0.5^a$ | 0 |
| 26,26,26-27,27,27-$F_6$-1,25-$(OH)_2D_3$ | 3.25 | $8.8 \pm 1.1^b$ | $2.4 \pm 0.2^b$ | 0–1 |
| | 13 | $7.6 \pm 1.1^c$ | $4.0 \pm 0.1^c$ | $\geq 5$ |
| 1,25-$(OH)_2D_3$ | 3.25 | $7.1 \pm 0.9^d$ | $2.5 \pm 0.4^d$ | 0 |
| | 13 | $9.6 \pm 2.1^e$ | $3.1 \pm 0.1^e$ | $1.3 \pm 1.1$ |
| Significance of Difference: | | a from b,c,d, & e $p < 0.001$ b from d N.S. c from e N.S. | a from b & d $p < 0.025$ a from c & e $p < 0.001$ c from e $p < 0.001$ | |

*Standard deviation of the mean

Bone Calcium Mobilization

Rats that had been fed the low calcium (0.02% Ca), adequate phosphorus, vitamin D-deficient diet for 3 weeks were divided into 6 groups of 5–6 rats each and given respectively 65 pmol of either 26,26,26,27,27,27-$F_6$-1,25-$(OH)_2D_3$ or 1,25-$(OH)_2D_3$ dissolved in 0.05 ml 95% ethanol intrajugularly either 24 hr or 72 hr prior to sacrifice. Rats in the control groups were given the ethanol vehicle in the same manner. The rats were killed by decapitation and the blood was collected. It was centrifuged to obtain serum. 0.1 ml of serum was mixed with 1.9 ml of 0.1% lanthanum chloride solution and calcium concentration was measured with an atomic absorption spectrophotometer (Perkin-Elmer Model 214). As intake of calcium from the diet is negligibly low, the increase of serum calcium concentration in response to 26,26,26,27,27,27-$F_6$-1,25-$(OH)_2D_3$ or 1,25-$(OH)_2D_3$ reflects bone calcium mobilization ability of the compound. Results are shown in Table 2.

TABLE 2

Increase in serum calcium concentration in response to a single dose of 65 pmol 26,26,26,27,27,27-$F_6$-1,25-$(OH)_2D_3$ or 1,25-$(OH)_2D_3$ given 24 or 72 hr prior to sacrifice of rats on a low calcium diet

| Compound | serum calcium concentration (mg/100 ml) | |
|---|---|---|
| | 24 hr | 72 hr |
| ethanol | $3.7 \pm 0.1^{*a}$ | $3.7 \pm 0.1^a$ |
| 26,26,26,27,27,27-$F_6$-1,25-$(OH)_2D_3$ | $5.3 \pm 0.3^b$ | $4.4 \pm 0.2^b$ |
| 1,25-$(OH)_2D_3$ | $4.4 \pm 0.2^c$ | $3.9 \pm 0.2^c$ |
| Significance of Difference | a from b & c $p < 0.001$ b from c $p < 0.001$ | a from e N.S. a from b $p < 0.001$ b from c $p < 0.005$ |

*Standard deviation of the mean

It can be concluded from the foregoing data that in the vitamin D responsive systems of vitamin D-deficient animals 26,26,26,27,27,27-$F_6$-1,25-$(OH)_2D_3$ exhibits activity at least ten times greater than that of 1,25-$(OH)_2D_3$ the hormonal form of the vitamin and heretofore considered the most biologically potent vitamin D derivative.

The 26,26,26,27,27,27-$F_6$-1,25$(OH)_2D_3$ of this invention may be readily administered in sterile parenteral solutions by injection or intravenously or by alimentary canal in the form of oral dosages, or by suppository. Doses of from about 0.1 μg to about 2.5 μg per day are effective in obtaining the physiological calcium balance responses described and which are characteristic of vitamin D-like activity, with maintenance doses of about 0.1 μg to 1.0 μg being suitable.

Dosage forms of the compound can be prepared by combining them with a non-toxic pharmaceutically acceptable carrier as is well known in the art. Such carriers may be either solid or liquid such as, for example, corn starch, lactose, sucrose, peanut oil, olive oil, sesame oil and water. If a solid carrier is used the dosage forms of the compounds of the invention may be tablets, capsules, powders, troches or lozenges. If a liquid carrier is used, soft gelatin capsules, or syrup or liquid suspension, emulsions or solutions may be the dosage form. The dosage forms may also contain adjuvants, such as preserving, stabilizing, wetting or emulsifying agents, solution promoters, etc. They may also contain other therapeutically valuable substances.

It should be understood that although dosage ranges are given the particular dose to be administered to a host will depend upon the specific disease state being treated and the end results being sought in a particular case, as well as other factors known to those skilled in the art in the therapeutic use of such medicinal agents.

We claim:

1. Compounds having the formula

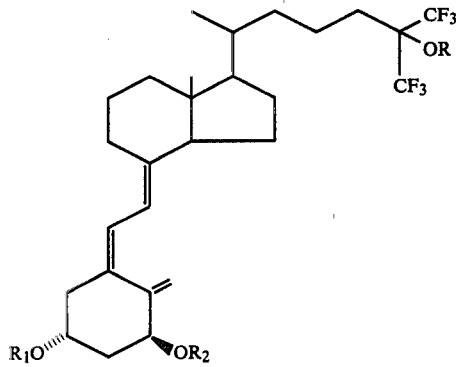

wherein R $R_1$ and $R_2$ are selected from hydrogen or acyl having from 1 to about 4 carbon atoms.

2. The compound of claim 1 where R, $R_1$ and $R_2$ are hydrogen.

3. The compound of claim 1 where R, $R_1$ and $R_2$ are acetyl groups.

4. The compound of claim 2 in a crystalline form.

5. 26,26,26,27,27,27-hexafluoro-1α,25-dihydroxycholesterol.

6. 26,26,26,27,27,27-hexafluoro-25-hydroxycholest-1,4-trien-3-one.

7. 26,26,26,27,27,27-hexafluoro-25-hydroxy-1α,2α-epoxycholest-4,6-dien-3-one.

8. 26,26,26,27,27,27-hexafluoro-1α,3β,25-trihydroxycholest-5,7-dien.

9. A method for preparing 26,26,26,27,27,27-hexafluoro-1α,25-dihydroxycholecalciferol which comprises hydrolyzing 26,26,26,27,27,27-hexafluoro-25-hydroxycholesterol-3-tetrahydropyranyl ether oxidizing the resulting 26,26,26,27,27,27-hexafluoro-25-hydroxycholesterol treating the resulting 26,26,26,27,27,27-hexafluoro-25-hydroxycholest-1,4,6-trien-3-one with hydrogen peroxide to obtain 26,26,26,27,27,27-hexafluoro-25-hydroxy-1α,2α-epoxycholest-4,6-dien-3-one reducing the said 1,2-epoxide with an alkali or alkaline earth metal in liquid ammonia or amine solvent to obtain 26,26,26,27,27,27-hexafluoro-1α,25-dihydroxycholesterol acetylating said 1α,25-dihydroxycholesterol to 26,26,26,27,27,27-hexafluoro-1α,25-dihydroxycholesterol triacetate converting said triacetate to 26,26,26,27,27,27-hexafluoro-1α,3β,25-triacetoxycholest-5,7-diene exposing said diene successively to ultraviolet radiation and thermal isomerization to obtain 26,26,26,27,27,27-hexafluoro-1α,25-dihydroxycholecalciferol triacetate hydrolyzing the said cholecalciferol triacetate to obtain 26,26,26,27,27,27-hexafluoro 1α,25-dihydroxycholecalciferol.

* * * * *